United States Patent [19]

Varma

[11] 4,160,772
[45] Jul. 10, 1979

[54] STEROIDAL[16α,17-D]CYCLOHEXENE-21-CARBOXYLIC ACID ESTERS

[75] Inventor: Ravi K. Varma, Belle Mead, N.J.

[73] Assignee: E. R. Squibb & Sons, Inc., Princeton, N.J.

[21] Appl. No.: 919,006

[22] Filed: Jun. 26, 1978

[51] Int. Cl.² ............................................. C07J 5/00
[52] U.S. Cl. ............................ 260/397.1; 260/397.45
[58] Field of Search ...................................... 260/397.1

[56] References Cited

U.S. PATENT DOCUMENTS 3,919,421  11/1975  Laurent et al. .................. 260/397.1
3,944,584  3/1976  Chao et al. ....................... 260/397.3

Primary Examiner—Elbert L. Roberts
Attorney, Agent, or Firm—Lawrence S. Levinson; Donald J. Barrack

[57] ABSTRACT

Steroids having the formula

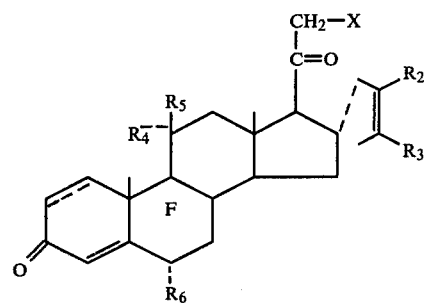

wherein $R_1$ is alkyl, aryl or arylalkyl; $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine; have useful antiinflammatory activity.

16 Claims, No Drawings

STEROIDAL[16α,17-D]CYCLOHEXENE-21-CARBOXYLIC ACID ESTERS

BACKGROUND OF THE INVENTION

Antiinflammatory activity, topical and systemic, is exhibited by many steroids of the pregnene series. More specifically, steroidal [16α,17-b] cyclohexenes having the formula

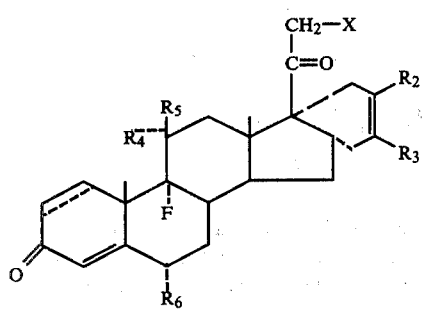

wherein X is hydrogen, hydroxy, halogen or acyloxy, and the "R groups" are as defined hereinafter, are disclosed as having topical and systemic antiinflammatory activity; see, for example, U.S. Pat. No. 3,944,584, issued Mar. 16, 1976.

The prior art also discloses various pregnene-21-oic acids and corresponding esters as having topical antiinflammatory activity, while being essentially inactive systemically. Exemplary disclosures are U.S. Pat. No. 3,919,421, issued Nov. 11, 1975; U.S. Pat. No. 3,956,347, issued May 11, 1976; U.S. Pat. No. 4,049,804, issued Sept. 30, 1977; and Laurent et al., *Journal of Steroid Biochemistry*, 6:185–192 (1975). One such pregnene derivative, fluocortin butyl ester (6α-fluoro-11β-hydroxy-16α-methyl-3,20-dioxopregna-1,4-diene-21-oic acid, butyl ester) has drawn particular attention and interest. Monder et al., *Journal of Steroid Biochemistry*, 8:897–908 (1977), discuss the synthesis of carboxylic acid derivatives of steroids, and the existence of these derivatives as metabolites of steroids.

SUMMARY OF THE INVENTION

Steroids having the formula

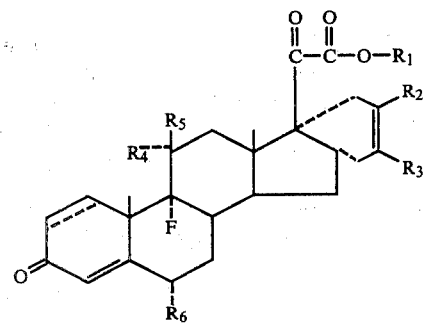

are useful as topical antiinflammatory agents. In formula I, and throughout the specification, the symbols are as defined below:

$R_1$ is alkyl of 1 to 10 carbon atoms, aryl or arylalkyl;

$R_2$ and $R_3$ are the same or different and are hydrogen, alkyl or aryl;

$R_4$ is hydrogen and $R_5$ is hydroxy or together $R_4$ and $R_5$ are =O; and $R_6$ is hydrogen, methyl or fluorine. The dotted lines in the 1,2-position of the steroids of this invention represent the optional presence of ethylenic unsaturation.

The term "aryl", as used throughout the specification, refers to phenyl or phenyl substituted with one or more halogen, alkyl and alkoxy groups.

The terms "alkyl" and "alkoxy", as used throughout the specification (unless otherwise defined), refer to both branched and straight chain groups having 1 to 8 carbon atoms. Groups having 1 to 4 carbon atoms are preferred.

The term "halogen", as used throughout the specification refers to fluorine, chlorine, bromine and iodine.

DETAILED DESCRIPTION OF THE INVENTION

The steroids of formula I can be prepared from the corresponding 21-hydroxysteroidal[16α,17-d]cyclohexenes having the structural formula

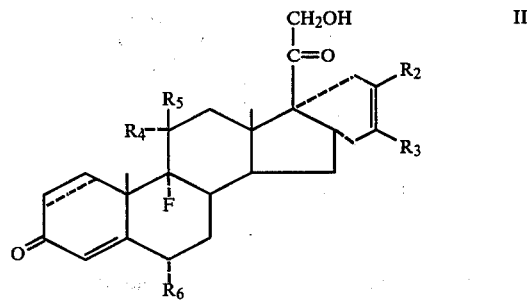

The steroids of formula II are known in the art; see, for example, U.S. Pat. No. 3,944,584 issued Mar. 16, 1976 to Varma et al.

A steroid of formula II can be oxidized to the corresponding aldehyde having the formula

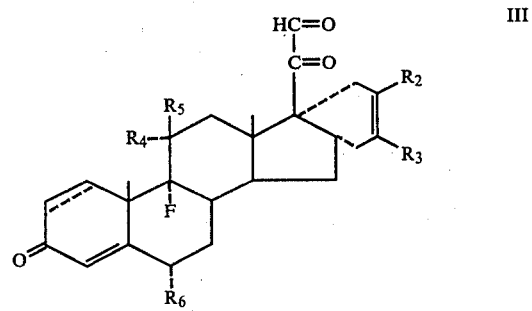

using a catalyst such as copper acetate. The reaction can be run in an alcohol solvent.

If the above described oxidation reaction is carried out in the presence of oxygen (e.g., by bubbling air through the reaction mixture), the reaction will generally yield, in addition to a steroidal-21-aldehyde of formula III, the corresponding steroidal-21-acetal formed with the alcohol solvent ($R_1$—OH); i.e., a steroid having the formula

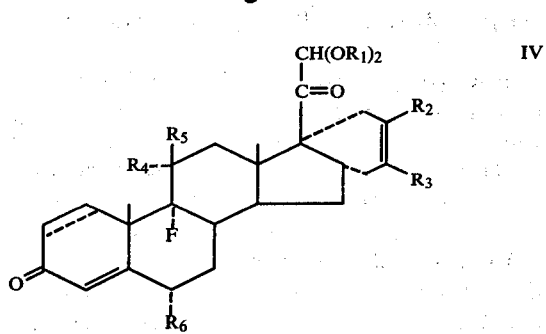

The oxidation reaction will generally be completed within a relatively short period of time, i.e., about 1 hour.

If the above-described reation is allowed to proceed for an extended period of time, e.g., more than about 24 hours, the major product will be the 20-hydroxy-21-carboxylic acid ester having the formula

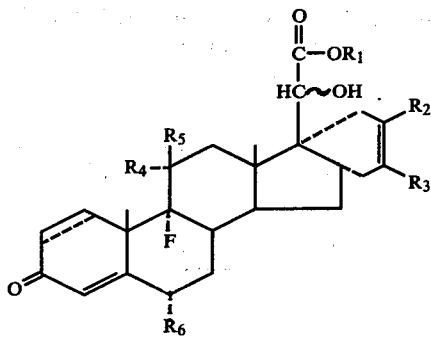

If water is present as a co-solvent in the oxidation reaction, and the reaction is allowed to proceed for an extended period of time, in addition to the 20-hydroxy-21-carboxylic acid ester of formula V, the corresponding 20-hydroxy-21-carboxylic acid will be produced; i.e., a steroid having the formula

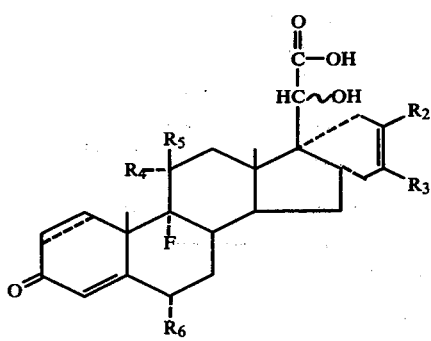

The steroids of formulas V and VI exist as mixtures of the 20α- and 20β-hydroxy-steroids.

A product of formula I can be obtained by reacting a mixture of a steroidal-21-aldehyde of formula III and the corresponding steroidal-21-acetal of formula IV with a mixture of (i) an inorganic cyanide catalyst (e.g., an alkali metal cyanide such as potassium cyanide); (ii) an oxidizing agent, e.g., a heavy metal oxide such as activated manganese dioxide or lead dioxide; (iii) an inert solvent, e.g., a halogenated hydrocarbon solvent such as dichloromethane or chloroform; (iv) a primary or secondary alcohol, $R'_1$—OH (throughout the specification $R'_1$ is any nontertiary $R_1$ group); and (v) an acid, e.g., acetic acid, which serves to neutralize the alkali cyanide catalyst. The products of the above reaction have the formula

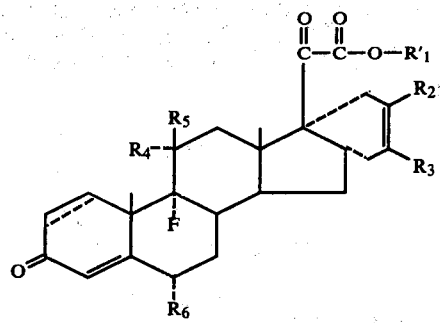

The 20α- and 20β-hydroxysteroids of formulas V and VI can be oxidized to obtain the corresponding 20-ketosteroids, having the respective formulas

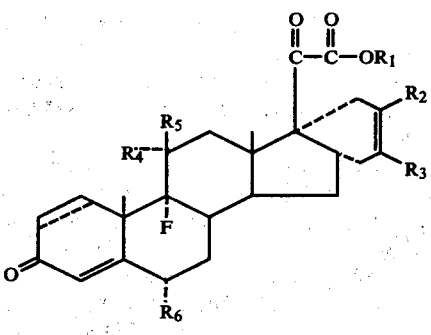

and

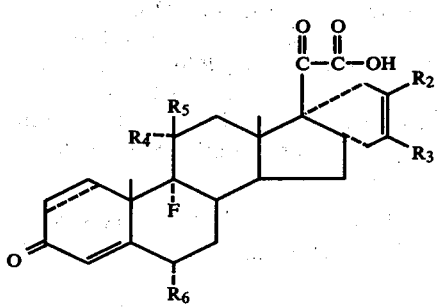

Examplary of suitable oxidizing agents are manganese dioxide and chromium dioxide. In the instance wherein the 20α- and 20β-hydroxysteroids being oxidized have an 11β-hydroxy substituent, the products of formulas I and VIII will be mixtures of 11β-hydroxy and 11-keto steroids.

The products of formula I can also be prepared by esterification of the corresponding steroidal-21-oic acid of formula VIII. (A steroid of formula VIII can be prepared as described above, or alternatively, by saponification of a corresponding steroidal-21-oic acid ester of formula I.)

Still another route for the preparation of the products of formula I wherein $R_1$ is a non-tertiary group is the transesterification of another ester of formula I. The starting steroid is reacted with the appropriate alcohol in the presence of a basic alkoxide (e.g., sodium ethoxide or aluminum isopropoxide) or, preferably, a source of cyanide ion (e.g., an alkali metal cyanide such as sodium cyanide or potassium cyanide) to yield the transesterification product.

The steroids of formula I are useful topical antiinflammatory agents which can be used in lieu of known glucocorticoids in the treatment of conditions such as dermatitis, psoriasis, sunburn, neurodermatitis, eczema and anogenital pruritus. The steroids may be administered in a conventional cream, ointment, lotion or spray in the range of 0.01 to 5.0% by weight, preferably 0.025 to 2.0% by weight.

The steroids of formulas III, IV, V, VI, and VIII are novel compounds that are useful in the preparation of the steroids of formula I; as such, they form an integral part of this invention.

The following examples are specific embodiments of this invention.

EXAMPLE 1

9-Fluoro-11β-hydroxy-3,20-dioxopregna-1,4-dieno[1-6α,17-d]cyclohexen-21-oic acid, methyl ester A solution of 1.2 g of 9-fluoro-11β,21-dihydroxypregna-1,4-dieno[16α,17-d]cyclohexene-3,20-dione and 300 mg of copper acetate in 150 ml of methanol is stirred at room temperature for 1 hour while a stream of air is bubbled through the solution. The solvent is evaporated in vacuo at 30° C. The residue is diluted with water and extracted with chloroform, and then, ethyl acetate. The chloroform solution and ethyl acetate solution are washed with aqueous ammonium chloride solution (10%) and water, dried over anhydrous sodium sulfate, evaporated in vacuo and combined to give 1.3 g of a solid. The NMR spectrum of the solid shows that it is an approximately equimolar mixture of the 21-aldehyde and 21-dimethylacetal derivatives of the starting steroid.

The solid product of the above reaction (1.3 g) is stirred in a mixture of 50 ml dry methanol and 50 ml dry dichloromethane at room temperature for about 16 hours with activated manganese dioxide (2.0 g), glacial acetic acid (1.0 ml) and potassium cyanide (200 mg). The suspension is filtered through a bed of Hyflo and washed with chloroform. The filtrate and washings are combined, washed with water and dried over anhydrous magnesium sulfate. The solvent is evaporated in vacuo to give 1.1 g of a solid. This is dissolved in chloroform and chromatographed on a 35 g-silica gel column. Elution with chloroform gives 930 mg of material. Crystallization from acetone-hexane gives 650 mg of the title compound, melting point 256°–258° C., with consistent spectra data.

Analysis Calc'd for $C_{28}H_{31}FO_5$: C, 70.57; H, 7.06; F, 4.29. Found: C, 70.66; H, 7.11; F, 4.02.

EXAMPLE 2

9-Fluoro-11β-hydroxy-3,20-dioxopregna-1,4-dieno[1-6α,17-d]cyclohexen-21-oic acid, 1-methylethyl ester A solution of 480 mg of 9-fluoro-11β-hydroxy-3,20-dioxopregna-1,4-dieno[16α,17-d] cyclohexen-21-oic acid, methyl ester (see Example 1) and 85 mg of sodium cyanide in 65 ml of dry isopropyl alcohol is stirred under a nitrogen atmosphere at 100° C. for about 16 hours. The resulting solution is evaporated in vacuo and the residue is dissolved in chloroform and washed with 25 ml of water. The aqueous layer is saturated with sodium chloride and extracted with chloroform. The chloroform solutions are combined, dried over anhydrous sodium sulfate and evaporated in vacuo. The residue is dissolved in chloroform-hexane (7:3) and chromatographed on a 25 g-silica gel column. Elution with chloroform-hexane (7:3) gives 370 mg of material. Crystallization from acetone-hexane gives 300 mg of the title compound, melting point 226°–228° C., with consistent spectral data.

Analysis calc'd for $C_{28}H_{35}FO_5$: C, 71.46; H, 7.50; F, 4.04. Found: C, 71.47; H, 7.44; F, 3.82.

EXAMPLE 3

9-Fluoro-11β-hydroxy-3,20-dioxopregna-1,4-dieno[1-6α,17-d]cyclohexen-21-oic acid, butyl ester A mixture of 1.0 g of 9-fluoro-11β,21-dihydroxypregna-1,4-dieno[16α,17-d]cyclohexene-3,20-dione and 250 mg of copper acetate in 50 ml of dichloromethane and 30 ml of n-butanol is stirred at room temperature for 1 hour while a slow stream of air is bubbled through the solution. Since the rate of oxidation is extremely slow, the dichloromethane is evaporated and replaced with 50 ml of n-butanol. Another 200 mg of copper acetate is added and the reaction is continued for 1.5 hour when the starting material disappears. The solvent is then evaporated in vacuo at 35°–40° C. and the residue is diluted with 200 ml of water and extracted with dichloromethane, and then ethyl acetate. The dichloromethane solution and ethyl acetate solution are washed with ammonium chloride solution (10%) and water, combined, dried over anhydrous sodium sulfate and evaporated in vacuo to give 1.2 g of solid. The NMR spectrum of the solid shows that it is an approximately equimolar mixture of the 21-aldehyde and 21-di-n-butylacetal derivatives of the starting steroid.

The solid product of the above reaction (1.2 g) is dissolved in 50 ml of dry dichloromethane and 30 ml of dry n-butanol and stirred at room temperature for about 16 hours with 2.0 g of activated manganese dioxide, 1.0 ml of glacial acetic acid and 200 mg of potassium cyanide. A dry calcium chloride tube is attached to the flask to avoid contact with moisture. After 20 hours another 2.0 g of activated manganese dioxide and 200 mg of potassium cyanide are added. The suspension is stirred at room temperature for 7 hours, filtered through a bed of Hyflo, and washed thoroughly with dichloromethane. The filtrate and washings are combined and washed with a saturated sodium bicarbonate solution and water, dried over anhydrous sodium sulfate and evaporated in vacuo. The title compound in the residue cannot be successfully separated from impurities on precoated silica gel TLC plate. It can, however, be successfully purified on E. Merck precoated silica gel TLC plate (2 mm, 2.5:97.5 methanol-chloroform) to give 400 mg of a foam. Crystallization from ethyl acetate-hexane gives 330 mg of the title compound, melting point 203°–209° C., with consistent spectra data.

Analysis calc'd for $C_{29}H_{37}FO_5$: C, 71.87; H, 7.70; F, 3.92. Found: C, 71.98 H, 7.73 F, 3.62.

EXAMPLE 4

9-Fluoro-11β-hydroxy-1',2'-dimethyl-3,20-dioxopregna-1,4-dieno[16α,17-d]cyclohexen-21-oic acid, methyl ester A solution of 4.9 g of 9-fluoro-11β,21-dihydroxy-1',2'-dimethyl-3,20-dioxopregna-1,4-dieno[16α,17-d] cyclohexene and 1.1 g of copper acetate in 800 ml of methanol is reacted with air following the procedure described in Example 1 (first paragraph) to yield 5.0 g of an approximately equimolar mixture of the 21-aldehyde and 21-dimethylacetal derivatives of the starting steroid.

The solid product of the above reaction (4.5 g) is stirred in a mixture of 250 ml dry methanol and 250 ml dry dichloromethane at room temperature for about 16 hours under a nitrogen atmosphere with activated manganese dioxide (7.0 g), glacial acetic acid (4.0 ml) and potassium cyanide (700 mg). The resulting suspension is filtered through a bed of diatomaceous earth and washed with chloroform-methanol (9:1). The filtrate and washings are combined and evaporated in vacuo to give 5.6 g of a solid. This is dissolved in chloroform-hexane (9:1) and chromatographed on a 100 g silica gel column. Elution with chloroform-hexane (9:1) yields 4.2 g of material, 1.5 g of which is crystallized from acetone-hexane to give 900 mg of an analytical specimen of the title compound, melting point 256°–258° C.

Analysis Calc'd for $C_{28}H_{35}FO_5$: C, 71.46; H, 7.50; F, 4.04. Found: C, 71.38; H, 7.50; F, 3.95.

EXAMPLE 5

9-Fluoro-11β-hydroxy-1',2'-dimethyl-3,20-dioxopregna-1,4-dieno[16α,17-d]cyclohexen-21-oic acid, ethyl ester (A)

9-Fluoro-11β-hydroxy-1',2'-dimethyl-3,20-dioxopregna, 1,2-dieno[16α,17-d]cyclohexen-21-oic acid A solution of 9-fluoro-11β-hydroxy-1',2', dimethyl-3,20-dioxopregna-1,4-dieno[16α,17-d] cyclohexen-21-oic acid, methyl ester (2.5 g) in a mixture of methanol (110 ml) and tetrahydrofuran (200 ml) is stirred with a solution of potassium hydroxide (640 mg) in water (10 ml) for 1.0 hour under a nitrogen atmosphere. The reaction mixture is then acidified with 5% hydrochloric acid and is evaporated in vacuo. The resulting slurry is mixed with water and filtered to afford 700 mg of the title compound, melting point 234°–238° C.

The filtrate is evaporated in vacuo and washed with chloroform-methanol (4:1). The solvents are evaporated to afford 1.4 g of the hydrated form of the title compound, melting point 215°–240° C.

(B)

9-Fluoro-11β-hydroxy-1',2'-dimethyl-3,20-dioxopregna-1,4-dieno[16α,17-d] cyclohexen-21-oic acid, ethyl ester To a suspension of 235 mg of 9-fluoro-11β-hydroxy-1',2'-dimethyl-3,20-dioxopregna-1,4-dieno [16α,17-d]cyclohexen-21-oic acid in 5.0 ml of dry dichloromethane is added successively, 0.5 ml of triethylamine and 0.068 ml of pivaloyl chloride. After the resulting solution is stirred at room temperature for 15 minutes, 0.116 ml of absolute ethanol is added. After 3.0 hours, the mixture is acidified with 50% hydrochloric acid, poured into water and extracted with chloroform. The chloroform extracts are combined, washed with water, dried over anhydrous magnesium sulfate, and evaporated. The residue is subjected to preparative thin-layer chromatography to isolate 97 mg of the title compound, melting point 198°–200° C.

EXAMPLE 6

9-Fluoro-11β-hydroxy-1',2'-dimethyl-3,20-dioxopregna-1,4-dieno [16α,17-d]cyclohexen-21-oic acid, 1,1-dimethylethyl ester A solution of 700 mg of 9-fluoro-11β-hydroxy-1',2'-dimethyl-3,20-dioxopregna-1,4-dieno [16α,17-d]cyclohexen-21-oic-acid (see Example 5A) in 60 ml of dry dioxane containing 12 ml of isobutylene and 0.7 ml of a sulfuric acid/phosphoric acid catalyst (prepared by adding phosphorous pentoxide to 96% sulfuric acid) is maintained in a pressure reaction vessel at room temperature for 24 hours. A stream of dry nitrogen is then passed through the solution to remove the excess isobutylene and the mixture is poured into a saturated sodium bicarbonate solution. The steroid is isolated by extraction with chloroform and the chloroform solution is washed with water, dried over anhydrous magnesium sulfate and the solvents are evaporated. The residue (760 mg) is subjected to chromatography on a column of silica gel to isolate 500 mg of the title compound, melting pount 209°–210° C. after crystallization from acetone-hexane.

EXAMPLE 7

9-Fluoro-11β-hydroxy-3,20-dioxopregna-1,4-dieno[16α,17-d]cyclohexen-21-oic acid, 2,2-dimethylpropyl ester A solution of 9-fluoro-11β-hydroxy-3,20-dioxopregna-1,4-dieno-[16α,17-d]cyclohexen-21-oic acid, methyl ester (25 mg) in dry dioxane (2.0 ml) containing dry neopentyl alcohol (400 mg) and sodium cyanide (5.0 mg) is refluxed under anhydrous conditions for 2.0 hours. The mixture is then cooled, added to water, and extracted with chloroform. The chloroform extract is washed with water, dried over anhydrous magnesium sulfate, evaporated and the residue is crystallized from ethyl acetate-chloroform to afford 23 mg. of the title compound, melting point 288° C. (dec., discoloration starts before melting point).

What is claimed is:

1. A steroid having the formula

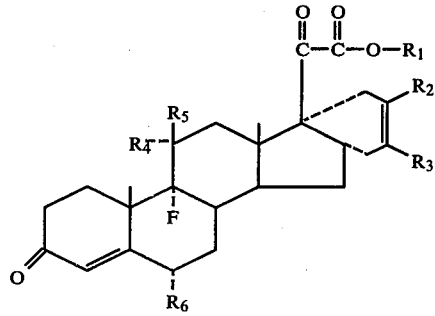

or the 1,2-dehydro derivative thereof, wherein $R_1$ is alkyl of 1 to 10 carbon atoms, aryl or arylalkyl; $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine.

2. A steroid in accordance with claim 1 wherein $R_4$ is hydrogen and $R_5$ is hydroxy, and $R_6$ is hydrogen.

3. A steroid in accordance with claim 1 wherein $R_1$ is alkyl of 1 to 10 carbon atoms.

4. A steroid in accordance with claim 1 wherein $R_1$ is aryl.

5. A steroid in accordance with claim 1 wherein $R_1$ is arylalkyl.

6. The steroid in accordance with claim 1 having the name 9-fluoro-11$\beta$-hydroxy-3,20-dioxopregna-1,4-dieno[16$\alpha$,17-d]cyclohexen-21-oic acid, methyl ester.

7. The steroid in accordance with claim 1 having the name 9-fluoro-11$\beta$-hydroxy-3,20-dioxopregna-1,4-dieno[16$\alpha$,17-d]cyclohexen-21-oic acid, 1-methylethyl ester.

8. The steroid in accordance with claim 1 having the name 9-fluoro-11$\beta$-hydroxy-3,20-dioxopregna-1,4-dieno[16$\alpha$,17-d]cyclohexen-21-oic acid, butyl ester.

9. The steroid in accordance with claim 1 having the name 9-fluoro-11$\beta$-hydroxy-1',2'-dimethyl-3,20-dioxopregna-1,4-dieno[16$\alpha$,17-d]cyclohexen-21-oic acid, methyl ester.

10. The steroid in accordance with claim 1 having the name 9-fluoro-11$\beta$-hydroxy-1',2'-dimethyl-3,20-dioxopregna-1,4-dieno[16$\alpha$,17-d]cyclohexen-21-oic acid, ethyl ester.

11. The steroid in accordance with claim 1 having the name 9-fluoro-11$\beta$-hydroxy-3,20-dioxopregna-1,4-dieno[16$\alpha$,17-d]cyclohexen-21-oic acid, 2,2-dimethylpropyl ester.

12. The steroid in accordance with claim 1 having the name 9-fluoro-11$\beta$-hydroxy-1',2'-dimethyl-3,20-dioxopregna-1,4-dieno[16$\alpha$,17-d] cyclohexen-21-oic acid, 1,1-dimethylethyl ester.

13. A steroid having the formula

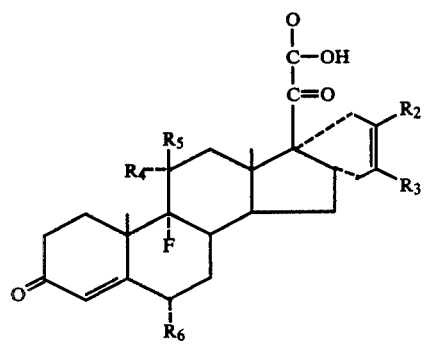

or the 1,2-dehydro derivative thereof, wherein $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine.

14. A steroid having the formula

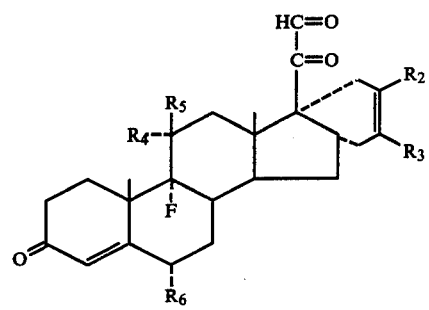

or the 1,2-dehydro derivative thereof, wherein $R_1$ is alkyl of 1 to 10 carbon atoms, aryl or arylalkyl; $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine.

15. A steroid having the formula

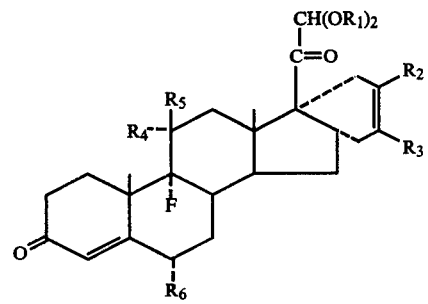

or the 1,2-dehydro derivative thereof, wherein $R_1$ is alkyl of 1 to 10 carbon atoms, aryl or arylalkyl; $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine.

16. A steroid having the formula

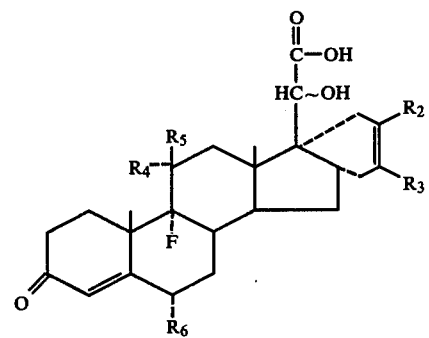

or

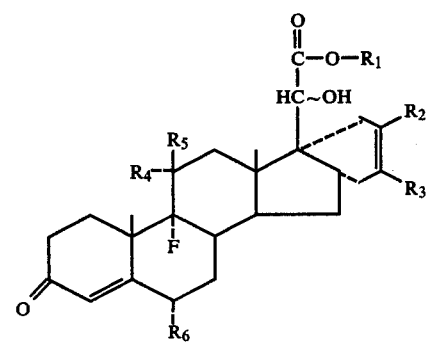

or the 1,2-dehydro derivative thereof, wherein $R_1$ is alkyl of 1 to 10 carbon atoms, aryl or arylalkyl; $R_2$ and $R_3$ are the same or different and are hydrogen, alkyl or aryl; $R_4$ is hydrogen and $R_5$ is hydroxy or together $R_4$ and $R_5$ are =O; and $R_6$ is hydrogen, methyl or fluorine.

* * * * *

UNITED STATES PATENT AND TRADEMARK OFFICE
CERTIFICATE OF CORRECTION

PATENT NO. : 4,160,772
DATED : July 10, 1979
INVENTOR(S) : Ravi K. Varma

It is certified that error appears in the above-identified patent and that said Letters Patent are hereby corrected as shown below:

The formula in the Abstract should read:

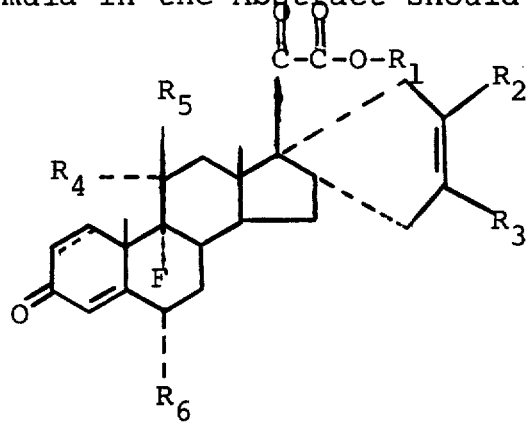

Col. 7, line 31, "1,2-dieno" should read -- 1,4-dieno --.

Signed and Sealed this

Ninth Day of October 1979

[SEAL]

Attest:

RUTH C. MASON
Attesting Officer

LUTRELLE F. PARKER
Acting Commissioner of Patents and Trademarks